United States Patent
Gentles et al.

(10) Patent No.: US 7,593,918 B2
(45) Date of Patent: Sep. 22, 2009

(54) ENTERPRISE MEDICAL IMAGING AND INFORMATION MANAGEMENT SYSTEM WITH ENHANCED COMMUNICATIONS CAPABILITIES

(75) Inventors: Thomas A. Gentles, Algonquin, IL (US); Prakash Mahesh, Schaumburg, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 434 days.

(21) Appl. No.: 11/039,153

(22) Filed: Jan. 19, 2005

(65) Prior Publication Data

US 2006/0112069 A1 May 25, 2006

Related U.S. Application Data

(60) Provisional application No. 60/631,044, filed on Nov. 24, 2004.

(51) Int. Cl.
*G06F 17/30* (2006.01)
(52) U.S. Cl. .......................................... 707/1; 707/101
(58) Field of Classification Search ...................... 707/1
See application file for complete search history.

(56) References Cited

U.S. PATENT DOCUMENTS

| 5,715,823 | A | * | 2/1998 | Wood et al. ................. 600/437 |
| 6,018,713 | A | * | 1/2000 | Coli et al. ....................... 705/2 |
| 6,024,699 | A | * | 2/2000 | Surwit et al. ................ 600/300 |
| 6,678,703 | B2 | * | 1/2004 | Rothschild et al. .......... 707/201 |
| 2001/0031997 | A1 | * | 10/2001 | Lee ............................. 607/59 |
| 2001/0050610 | A1 | * | 12/2001 | Gelston ..................... 340/5.53 |

(Continued)

FOREIGN PATENT DOCUMENTS

DE        101 57 788 A1     6/2003

(Continued)

OTHER PUBLICATIONS

Pavlovski, et al., "Ubiquitous Mobility in Clinical Healthcare," Medical Information Systems: The Digital Hospital, 2004. Ideas '04-DH. Proceedings. Ideas Workshop on Beijing, China Sep. 1-3, 2004. Piscataway, NJ, USA, IEEE, Sep. 1, 2004 pp. 147-153, XP010779140.
International Search Report for EP 05 25 7194 (Feb. 2, 2006).

*Primary Examiner*—Don Wong
*Assistant Examiner*—Binh V Ho
(74) *Attorney, Agent, or Firm*—Hanley, Flight & Zimmerman, LLC

(57) ABSTRACT

Certain embodiments of the present invention provide improved clinical workflow using a medical imaging and information management system and method with enhanced communication capabilities. Certain embodiments of the system include an information manager including clinical content, such as images and/or information, and a communication manager receiving an event notification from the information manager. The system may further include an interface capable of accessing the information manager. Additionally, the system may include a contact device capable of communicating via the communication manager. A modality may transmit examination data to the information manager and may receive instructions for the information manager. In an embodiment, the communications manager includes a contact information list with one or more contact devices associated with a user. The communications manager may be capable of detecting a presence of a user on a network.

6 Claims, 2 Drawing Sheets

U.S. PATENT DOCUMENTS

| | | |
|---|---|---|
| 2002/0002483 A1* | 1/2002 | Siegel et al. .................. 705/10 |
| 2002/0007398 A1* | 1/2002 | Mendiola et al. ............ 709/206 |
| 2002/0059587 A1* | 5/2002 | Cofano et al. ................. 725/35 |
| 2003/0028399 A1* | 2/2003 | Davis et al. .................... 705/2 |
| 2004/0128165 A1* | 7/2004 | Block et al. .................... 705/2 |
| 2005/0143671 A1* | 6/2005 | Hastings et al. ............. 600/513 |
| 2006/0080151 A1* | 4/2006 | Barbash ......................... 705/3 |

FOREIGN PATENT DOCUMENTS

| | | |
|---|---|---|
| EP | 1 418 525 | 5/2004 |
| WO | WO 2004/042596 | 5/2004 |
| WO | WO 2005/076982 A2 * | 8/2005 |

* cited by examiner

ENTERPRISE MEDICAL IMAGING AND INFORMATION MANAGEMENT SYSTEM WITH ENHANCED COMMUNICATIONS CAPABILITIES

RELATED APPLICATIONS

The present application relates to, and claims priority from, U.S. Provisional Application No. 60/631,044 filed on Nov. 24, 2004, and entitled "Enterprise Medical Imaging and Information Management System with Enhanced Communications Capabilities".

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an image and information management system. In particular, the present invention relates to an image and information management system with enhanced communication capability.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

In a healthcare or clinical environment, such as a hospital, a large number of employees and patients may result in confusion or delay when trying to reach other medical personnel for examination, treatment, consultation, or referral, for example. A delay in contacting other medical personnel may result in further injury or death to a patient. Additionally, a variety of distractions in a clinical environment may frequently interrupt medical personnel or interfere with their job performance. Furthermore, workspaces, such as a radiology workspace, may become cluttered with a variety of monitors, data input devices, data storage devices, and communication devices, for example. Cluttered workspaces may result in inefficient workflow and service to clients, which may impact a patient's health and safety or result in liability for a healthcare facility.

Data entry and access is also complicated in a typical healthcare facility. Speech transcription or dictation is typically accomplished by typing on a keyboard, dialing a transcription service, using a microphone, using a Dictaphone, or using digital speech recognition software at a personal computer. Such dictation methods involve a healthcare practitioner sitting in front of a computer or using a telephone, which may be impractical during operational situations. Similarly, for access to electronic mail or voice messages, a practitioner must typically use a computer or telephone in the facility. Access outside of the facility or away from a computer or telephone is limited.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include clinical information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided among a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and/or ordering additional tests or consultation, for example. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitates operation of an imaging system and related services by an individual operator would be highly desirable.

Additionally, in a healthcare workflow, healthcare providers often consult or otherwise interact with each other. Such interaction typically involves paging or telephoning another practitioner. Thus, interaction between healthcare practitioners may be time- and energy-consuming. Therefore, there is a need for a system and method to simplify and improve communication and interaction between healthcare practitioners.

Furthermore, healthcare practitioners may want or need to review diagnoses and/or reports from another healthcare practitioner. For example, a referring physician may want to review a radiologist's diagnosis and report with the radiologist and/or a technician. As another example, an emergency room physician may need to review results of an emergency room study with the radiologist and/or a family physician. Thus, there is a need for a system and method for notifying or informing appropriate parties of results in order to collaborate for diagnosis and/or treatment review for safe and effective treatment.

Typically, healthcare practitioners determine each other's availability and schedule a collaboration event. Thus, current systems and methods require more manual involvement and multiple steps. Current systems encouraging interactions between healthcare practitioners consist of several discrete or manual actions involving a number of disparate systems and/or individuals. First, third parties are notified of information availability. Then, third parties obtain the information by accessing one or more systems. After a system verifies that the information has been received, the practitioner and third party must determine their availability for collaboration. After the parties schedule a mutually available time for collaboration, the parties may finally collaborate to review exam results, diagnosis, treatment, etc. The involvement of a plurality of disparate systems/parties and requirement of several disparate steps renders current systems and methods complicated, inefficient, and time consuming. An ability to reduce the number of actions required by interested parties, reduce the number of ineffective actions, and reduce the waiting time required to obtain necessary information and perform a collaboration would result in more efficient and effective healthcare delivery.

Thus, there is a need for a system and method to improve clinical workflow using an enhanced system and method for image management and communication.

BRIEF SUMMARY OF THE INVENTION

Certain embodiments of the present invention provide improved clinical workflow using a medical imaging and information management system and method with enhanced communication capabilities. Certain embodiments of the system include an information manager including clinical content and a communication manager receiving an event notification from the information manager. The clinical content may include images and/or information, for example. In an embodiment, the information manager includes a picture archiving and communications system, for example.

The system may further include an interface capable of accessing the information manager. Additionally, the system may include a contact device capable of communicating via the communication manager. A modality may transmit examination data to the information manager and may receive instructions from the information manager. In an embodiment, the communications manager includes a contact information list with one or more contact devices associated with a user. The communications manager may be capable of detecting a presence of a user on a network.

Certain embodiments of a method for improved medical workflow using an enhanced image management system include scheduling an examination, requesting a notification upon receipt of examination results, and automatically generating the notification upon receipt of the results. Examination may include examination of a patient using an image modality, for example. Examination results may be transmitted to an image manager. Notification may include an alert, a message, a report, an image, and/or a conference (e.g., a scheduled conference and/or an initiated conference), for example. Notification may include contacting a user via at least one of a telephone network and an internet protocol network, for example.

Certain embodiments include a computer-readable storage medium including a set of instructions for a computer. The set of instruments includes an image management routine receiving and storing image information and a communication management routine facilitating two-way communication between one or more users. The communication management routine initiates communication based on input from the image management routine and contact information.

In an embodiment, the communication management routine accesses a profile for each of the one or more users to initiate communication. The communication management routine may contact the one or more users via a telephone network and/or an internet protocol network, for example. The communication management routine may notify one or more users using an alert, a message, a report, an image, and/or a conference, for example. In an embodiment, the communication management routine monitors a network for a presence of a user.

The set of instructions may further include a scheduling routine for scheduling a conference based on input from the image management routine and the communication management routine. The set of instructions may also include an interface routine for providing order information, follow-up instructions, and results to the image management routine, for example.

Figure 1:
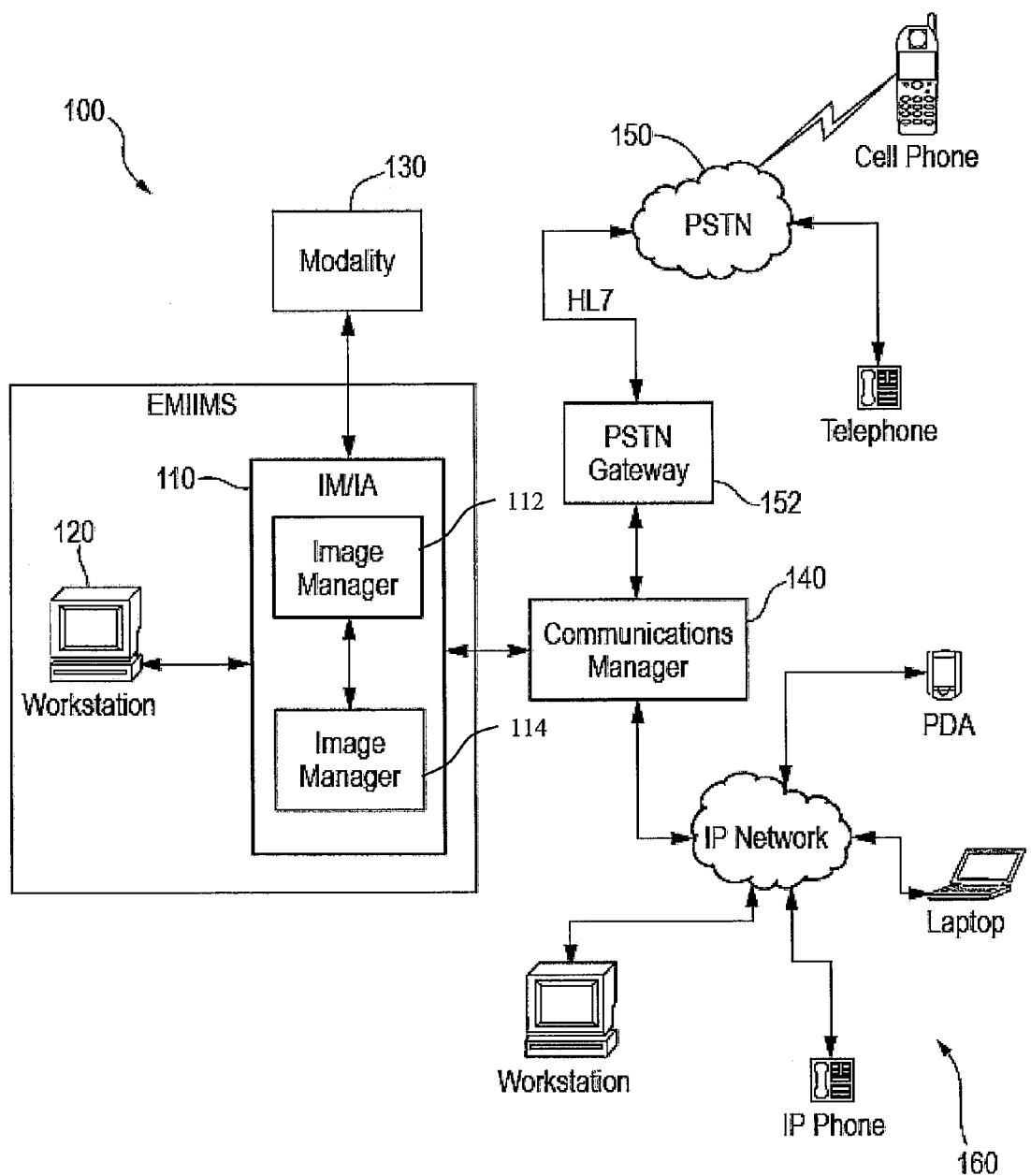
FIG. 1 illustrates a wireless voice communication system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an image management and communication system 100 used in accordance with an embodiment of the present invention. The system 100 includes an image management system 110, an interface 120, a modality 130, a communications manager 140, a telephone network 150, and an internet protocol (IP) network 160. The image management system 110 may include an image manager 112 and an image archive 114, for example.

In an embodiment, the image management and communication system 100 is a communications enabled enterprise medical imaging and information management system (CEEMIIMS). The CEEMIIMS combines capabilities of an image management system, an image archive system with integrated workflow and exam reading capabilities for a medical enterprise, for example. For example, the CEEMIIMS may be a Picture Archiving and Communication System (PACS) integrated with a communications manager.

The image management system 110 is capable of performing image management, image archiving, exam reading, exam workflow, and/or other medical enterprise workflow tasks, for example. In an embodiment, the system 110 is or includes a PACS, for example. The system 110 may also include a healthcare or hospital information system (HIS), a radiology information system (RIS), a clinical information system (CIS), a cardiovascular information system (CVIS), a library information system (LIS), order processing system, and/or an electronic medical record (EMR) system, for example. The image management system 110 may include an image manager 112 for image management and workflow. The image management system 110 may also include an image archive 114 for image storage and retrieval.

The interface 120, such as a workstation (e.g., a PACS workstation) or other data processing device (e.g., laptop, tablet computer, personal digital assistant, handheld computer, cellular phone, etc.), may be used to access (e.g., input and retrieve data) the system 110. The interface 120 may communicate with the image management system 110 via wired, wireless, and/or infrared communication, for example. Vocal/subvocal command and/or other forms of communication and control may be used to interface with the system 100. In an embodiment, a password and/or other authentication, such as voice or other biometric authentication, may be used to establish a connection between the system 110 and the interface 120. In an embodiment, the interface 120 may be integrated with the system 110.

The image management system 110 interacts with one or more modalities 130, such as an x-ray system, computed tomography (CT) system, magnetic resonance (MR) system, ultrasound system, digital radiography (DR) system, positron emission tomography (PET) system, single photon emission computed tomography (SPECT) system, nuclear imaging system, and/or other modality. The image management system 110 may acquire image data and related data from the modality 130 for processing and/or storage.

The image management system 110 is connected with the communications manager 140 via wired, wireless and/or infrared communication, for example. The communications manager 140 may be a separate system or may be integrated with the system 110, for example. The communications manager 140 may be a server, workstation, medical information system, and/or other computing system, for example. The communications manager 140 receives information from the system 110 and transmits information via a communication medium/device, such as a wired or wireless modem, cellular transmission, infrared transmission, Ethernet, fire wire, Internet, virtual private network, public switched telephone network, dial-up, local area network, and/or wide area network, for example.

The communications manager 140 may facilitate a plurality of functions, such as handling event notifications and requests from the image management system 110, managing contact information for a set of subscribers or members, providing notification to subscribers of events, managing calls for collaboration events, managing multi-media streams for collaboration events, and/or managing presence information and status for subscribers or members. The communications manager 140 handles communications tasks associated with notification, collaboration, and/or data transfer in a medical enterprise, for example.

The communications manager 140 may transmit information and/or notification to the telephone network 150 and/or the IP network 160, for example. The communications manager 140 may automatically schedule consultation calls. In an embodiment, the telephone network 150 is a public switched telephone network (PSTN) with a PSTN gateway 152, for example. The PSTN 152 gateway facilitates communication with the PSTN network including "landline" telephones and/or cellular phones, for example. The IP network 160 may facilitate communication with personal digital assistants (PDAs), laptops, IP telephones, and/or workstations, for example, transferring data according to Internet Protocol.

The image management system 110 may receive examination data, such as image data, and additional information from the modality 130 and/or the interface 120. Additional information may indicate findings within the image data, diagnosis information, treatment information, and/or consultation or referral information, for example. For example, a physician may add to an exam a note to notify him or her when results are available and to set up a call with a radiologist for review. The note may be transcribed from an order or exam into the image management system 110. For example, the order is processed in a hospital information structure and transferred to the image management system 110 (e.g., PACS). The request to notify/consult is identified in the system 110 based on certain rules, filters, and/or lexical analysis, for example. When exam images and/or radiology results, for example, are received at the image manager 110, the system 110 has the results, images, contact information for the radiologist, and contact information for the referring physician, for example. The system 110 sends a message to the communications manager 140 to notify the physician of the results and to set up a conference with the radiologist at a given time or at a time when all parties are available, for example.

The communications manager 140 may schedule a conference, such as a multimedia conference, based on provided contact information, such as contact information for the radiologist and for the referring physician. In an embodiment, the communications manager 140 includes call processing rules, input parameters, preferences, and/or other input information, for example. The manager 140 may schedule a call based on such information. For example, information/preferences may include specific times and/or time periods, location, type of communication (e.g., cell phone, computer, etc.), availability, etc.

The communications manager 140 may store profile(s) and/or contact information for members/subscribers, for example. The communications manager 140 may select one or more contact devices from a user's profile to initiate a communication (e.g., cellular phone, office phone, home phone, pager, laptop IP address, etc.). For example, the communications manager 140 may initiate a connection between the physician's cellular phone and the radiologist's workstation. Additionally, the communications manager 140 may save or have access to a calendar or schedule for each user.

The communications manager 140 may determine when a user is available and on what device, for example.

In an embodiment, the communications manager 140 may also look for a "presence" of a user in the system 100. That is, the communications manager 140 determines whether the user is registered or "logged in" in the healthcare environment. For example, the manager 140 may determine whether the referring physician has his or her cellular phone switched on. In an embodiment, a user may set presence parameters, such as available, away, busy, do not disturb except for certain occurrence(s), etc. For example, a surgeon may set his or her status to do not disturb except for emergencies when in surgery.

In operation, for example, the image management system 110 receives an order for a radiology exam. The order is tagged with information indicating that the exam includes a notification of a reading radiologist upon receipt of the exam by the image manager 110. At some point, the image manager 110 receives the exam from the modality 130. The image manager 110 then notifies the reading radiologist of the availability of the exam for reading. The notification occurs via an event that is sent to the communications manager 140 from the image manager 110 instructing the communications manager 140 to contact the radiologist with the information that the exam is available and information on how to access the exam, for example. The communications manager 140 contacts the radiologist based upon a prescribed set of rules that determine how the radiologist may be contacted. Contact may be achieved through data communication, such as over the IP network 160, and/or through telephone communication, such as the PSTN network 150. The type of contact client, such as a workstation, PDA, cell phone, etc., determines the type of information provided to the radiologist in the notification message, such as a reference to the exam, contact phone number or email address, meeting time, etc.

Figure 2:
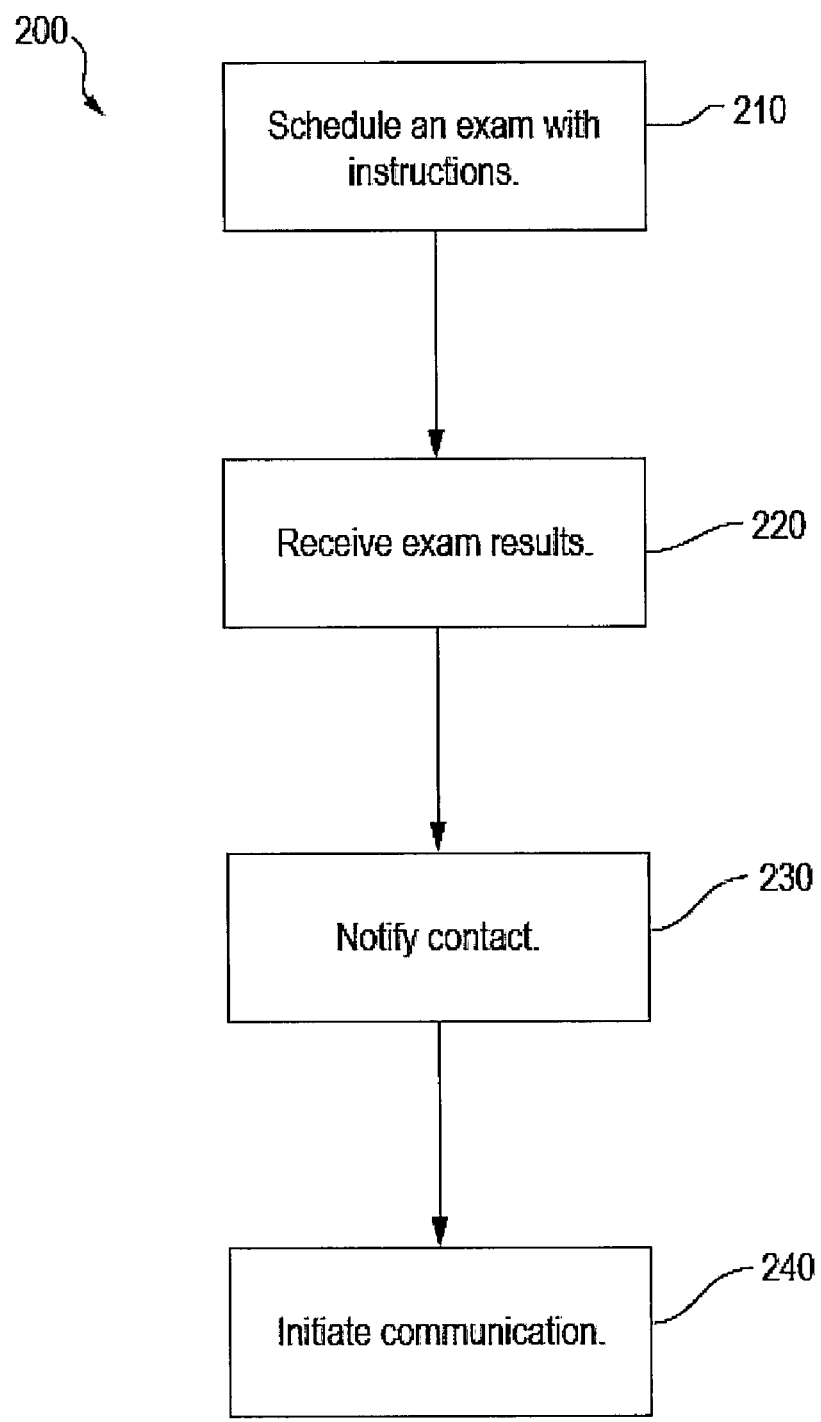
FIG. 2 depicts a flow diagram for a method for image management and communication used in accordance with an embodiment of the present invention.

FIG. 2 depicts a flow diagram for a method 200 for image management and communication used in accordance with an embodiment of the present invention. First, at step 210, an exam is scheduled. The schedule includes instructions in addition to the exam order. Instructions may include a request for notification of examination images and/or results, for example. Instructions may include a request for a conference or collaboration between healthcare practitioners, for example. For example, the image management system 110 is used to schedule a patient chest x-ray series with the modality 130. A conference request is also scheduled with the image management system 110 via the interface 120.

Next, at step 220, examination results are received. For example, x-ray images from a patient's chest x-ray series are transferred to the image management system 110 from the modality 130 (e.g., an x-ray system). Then, at step 230, the contact is notified. That is, a requesting party may be notified that exam results have arrived. The requesting party may be provided with a copy of the results. A second party may be notified of a conference with the requesting party to discuss the results. The second party may be provided with a copy of the examination results as well. In an embodiment, the contact(s) may be notified in advance to schedule a conference or review of results. For example, the communications manager 140 may check the schedules of the requesting party and the collaborating party to determine a commonly available time slot. Then, when examination results arrive, both parties are notified with a time (and possibly place) for the meeting.

At step 240, communication may be initiated between participating parties. Communication may be initiated through the communication manager 140 and the image management system 110 (and possibly interface 120), for example. The communication manager 140 may utilize the IP network 160 and/or the PSTN network 150 to connect one or more parties to each other and/or to the contents/capabilities of the image management system 110. In an embodiment, results of a conference or collaboration may be stored at the image management system 110.

Thus, certain embodiments provide increased efficiency in a medical workflow through improved communication and notification of examination results. For example, time is reduced from a modality scan until a radiologist is aware that an exam is available and warrants action. Certain embodiments provide increased efficiency because fewer steps are involved for a user of an image management and archive system to determine that an exam is available and warrants further action. Certain embodiments help enhance patient safety through a more robust notification mechanism that helps to insure that results and appropriate information or collaboration needs are scheduled and executed.

Certain embodiments provide integration of communication capabilities with an enterprise imaging and information management system in a healthcare environment. Certain embodiments provide communications capabilities and functions as an adjunct to more efficient workflow and enhanced ability to deliver healthcare services.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical imaging and information management system with enhanced communication capabilities, said system comprising:
    an information manager including clinical content, said clinical content including at least examination data transmitted to the information manager from a modality, wherein said modality is capable of receiving instructions from said information manager;
    a communication manager receiving an event notification regarding the clinical content from said information manager via a network,
    wherein said communications manager is adapted to detect a presence of a user on the network for communication, wherein said communication manager is adapted to initiate interactive electronic communication with a plurality of user contact devices via the network to facilitate electronic collaboration regarding the clinical content between said plurality of user contact devices based on said event notification, wherein users at said plurality of user contact devices electronically interact via the collaboration with respect to the clinical content, and wherein the medical imaging and information management system provides collaborators using the plurality of user contact devices with storage and management of said clinical content in conjunction with integrated workflow and image reading capabilities; and
    at least one workstation interfacing with at least one of the information manager and the communication manager.

2. The system of claim 1, wherein said clinical content comprises at least one of images and information.

3. The system of claim 1, further comprising an interface capable of accessing said information manager.

4. The system of claim 1, wherein said communications manager further comprises a contact information list including one or more contact devices associated with a user.

5. The system of claim 1, wherein said information manager comprises a picture archiving and communications system.

6. The system of claim 1, wherein said event notification comprises at least one of an indication of examination results, an alert, a message, a report, and an image.

* * * * *

UNITED STATES PATENT AND TRADEMARK OFFICE
CERTIFICATE OF CORRECTION

PATENT NO. : 7,593,918 B2
APPLICATION NO. : 11/039153
DATED : September 22, 2009
INVENTOR(S) : Gentles et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Twenty-eighth Day of September, 2010

David J. Kappos
*Director of the United States Patent and Trademark Office*